(12) United States Patent
Murata

(10) Patent No.: US 7,741,069 B2
(45) Date of Patent: Jun. 22, 2010

(54) MESOPOROUS MATERIAL HAVING DENDRITIC SKELETON CONTAINING IMMOBILIZED GLUCOSE DEHYDROGENASE

(75) Inventor: Yusuke Murata, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 804 days.

(21) Appl. No.: 11/567,974

(22) Filed: Dec. 7, 2006

(65) Prior Publication Data

US 2008/0020411 A1    Jan. 24, 2008

(30) Foreign Application Priority Data

Dec. 27, 2005  (JP)  ............... 2005-375173
Jun. 7, 2006   (JP)  ............... 2006-158635

(51) Int. Cl.
  *C12Q 1/32*   (2006.01)
  *C12Q 1/54*   (2006.01)
  *C12N 11/14*  (2006.01)
  *C12N 11/02*  (2006.01)
  *C12N 11/04*  (2006.01)

(52) U.S. Cl. ............. 435/26; 435/14; 435/176; 435/177; 435/182; 435/817

(58) Field of Classification Search .......... None
See application file for complete search history.

(56) References Cited

U.S. PATENT DOCUMENTS

| 5,624,875 | A | 4/1997 | Nakanishi et al. |
| 5,874,047 | A * | 2/1999 | Schoning et al. ......... 422/82.02 |
| 5,980,849 | A | 11/1999 | Ogata et al. |
| 6,696,258 | B1 * | 2/2004 | Wei et al. ................. 435/7.2 |
| 6,846,546 | B2 | 1/2005 | Kuroda et al. |
| 7,341,846 | B2 * | 3/2008 | Yamaoka et al. ............ 435/26 |
| 2002/0015985 | A1 | 2/2002 | Takahashi et al. |
| 2005/0048264 | A1 | 3/2005 | Miyata et al. |
| 2005/0249878 | A1 | 11/2005 | Miyata et al. |
| 2006/0062909 | A1 | 3/2006 | Miyata et al. |
| 2007/0196659 | A1 * | 8/2007 | Setoyama et al. ........... 428/408 |

FOREIGN PATENT DOCUMENTS

| JP | 6-265534 A | 9/1994 |
| JP | 10-087319 A | 4/1998 |
| JP | 2000-139459 A | 5/2000 |
| JP | 2002-95471 A | 4/2002 |
| JP | 2005-290032 A | 10/2005 |
| WO | 2005/080953 A | 9/2005 |

OTHER PUBLICATIONS

C. Jeffrey Brinker, Sol-Gel Science: The Physics and Chemistry of Sol-Gel Processing, Chapter 10, 617-72 (1990).

* cited by examiner

*Primary Examiner*—David M Naff
(74) *Attorney, Agent, or Firm*—Fitzpatrick, Cella, Harper & Scinto

(57) ABSTRACT

A porous material containing mesopores with immobilized glucose dehydrogenase is provided. The pore size is at least 10 nm.

9 Claims, 10 Drawing Sheets

1 μm 50 nm 50 nm

1 μm 100 nm

MESOPOROUS MATERIAL HAVING DENDRITIC SKELETON CONTAINING IMMOBILIZED GLUCOSE DEHYDROGENASE

BACKGROUND OF THE INVENTION

1. Field of the Invention

The present invention relates to porous materials with immobilized glucose dehydrogenase. The porous materials can be used in glucose sensors for detecting blood glucose levels by utilizing the characteristics of glucose dehydrogenase.

2. Description of the Related Art

Enzymes are readily inactivated by heat, which alters proteins constituting the enzymes. Consequently, in order to stably utilize enzymes, technologies for immobilizing them on pore walls of porous materials have been developed.

Among such technologies, mesoporous materials have been actively developed because they have large specific surface areas. Therefore, the amount of the immobilized enzyme per unit area can be increased (Japanese Patent Laid-Open Nos. 2000-139459 and 2002-95471).

However, pore sizes of existing mesoporous materials are small, and glucose dehydrogenase, which is large in size, cannot be immobilized on mesopore walls of these mesoporous materials.

The present invention provides a porous material with glucose dehydrogenase immobilized in its mesopores.

SUMMARY OF THE INVENTION

In order to solve the above-mentioned problems, the present invention provides a porous material containing mesopores having a pore size of at least about 10 nm. Glucose dehydrogenase is immobilized in the mesopores.

In addition, the present invention provides a composition including a porous material, glucose dehydrogenase, and an electron transfer material. The porous material contains mesopores having a pore size of 10 nm or more. The glucose dehydrogenase is immobilized on the mesopore walls. The electron transfer material receives electrons from a biological substance in the porous material.

Furthermore, the present invention provides a sensor including a porous material, glucose dehydrogenase, a buffer solution containing an electron transfer material, and an electrode. The porous material contains mesopores having a pore size of at least about 10 nm. The glucose dehydrogenase is immobilized on the mesopore walls. The electron transfer material receives electrons from a biological substance in the porous material. The electrode receives the electrons from the electron transfer material.

According to the present invention, a porous material containing mesopores with a pore size of 10 nm or more and with glucose dehydrogenase immobilized on the mesopore walls thereof is provided. Therefore, the porous material can be applied in a sensor using glucose dehydrogenase.

Further features of the present invention will become apparent from the following description of exemplary embodiments with reference to the attached drawings.

DESCRIPTION OF THE EMBODIMENTS

Figure 1:
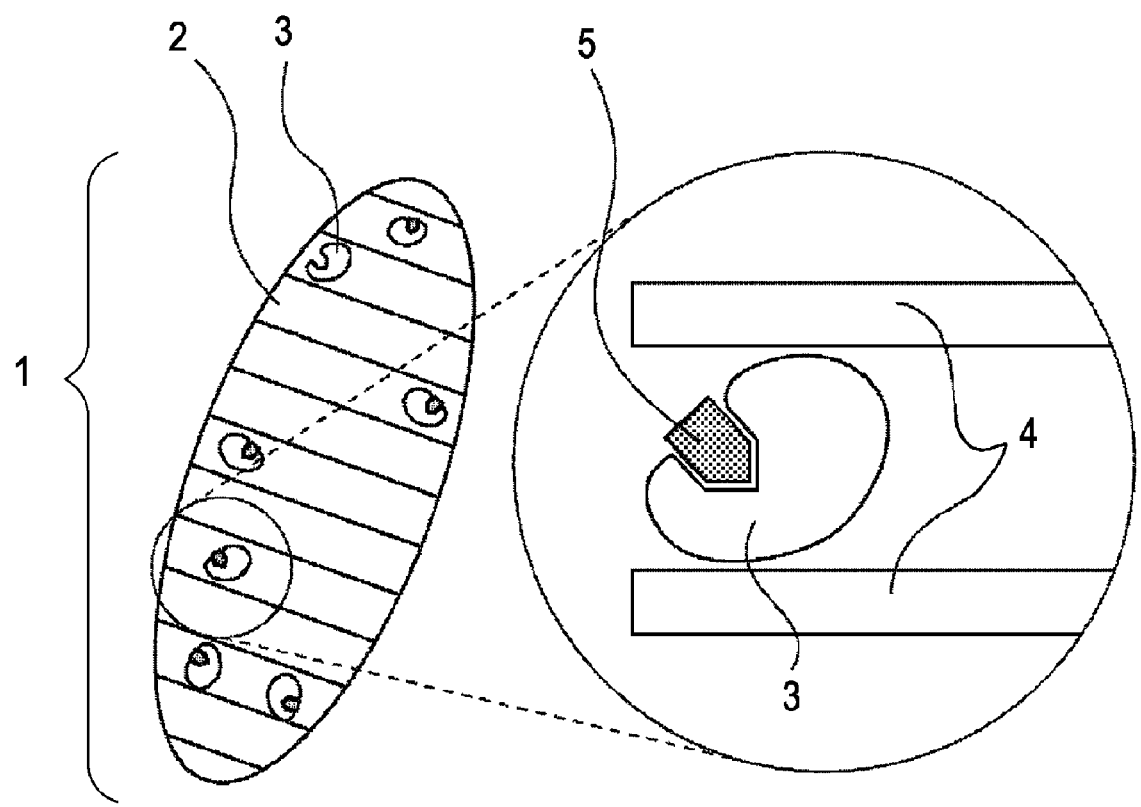
FIG. 1 is a schematic diagram illustrating a rod-shaped particle according to an embodiment of the present invention.
Figure 2:
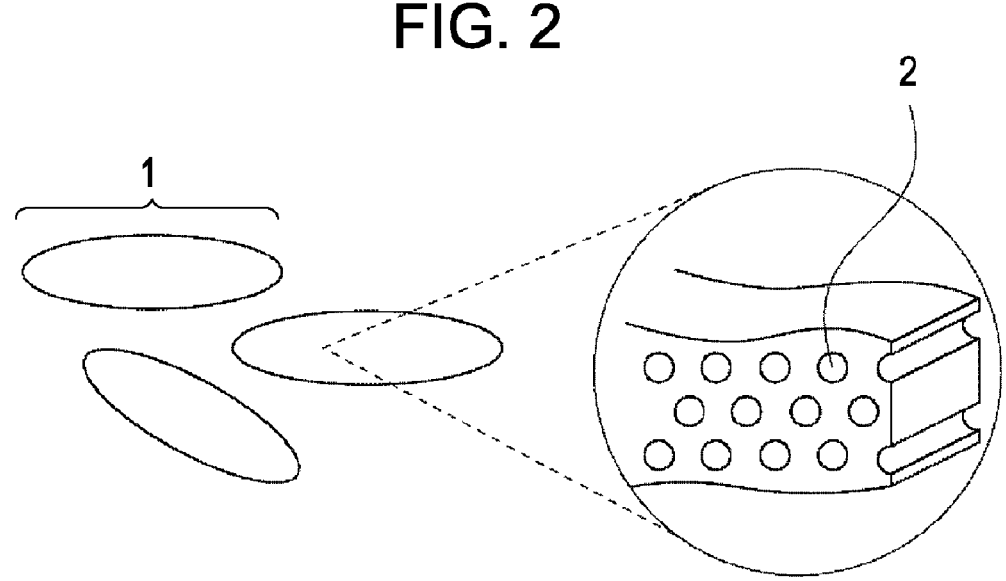
FIG. 2 is a schematic diagram illustrating a rod-shaped particle according to an embodiment of the present invention.

Several aspects of the present invention will be briefly described by referring to FIGS. 1 and 2. FIG. 1 shows a porous material 1 with immobilized glucose dehydrogenase (GDH) according to an embodiment of the present invention. In this example, the porous material 1 consists of rod-shaped particles. Each rod-shaped particle contains mesopores 2 that are formed in the minor axis direction of the rod-shaped particle. Glucose dehydrogenase 3 is immobilized in the mesopores 2. An enlarged view of a part of the porous material 1 with immobilized glucose dehydrogenase 3 is shown in FIG. 1. Pore walls 4 are represented by bars. Glucose dehydrogenase 3 is immobilized so as to be sandwiched by the pore walls 4. Glucose 5 is bound to an active site of the glucose dehydrogenase 3.

FIG. 2 is a schematic diagram of rod-shaped particles according to an embodiment of the present invention, viewed from a different angle. Individual particles of the porous material 1 with immobilized glucose dehydrogenase are represented by ellipses. An enlarged view of a part of the porous material 1 is shown in FIG. 2. Mesopores 2 are tube-shaped, and the openings of the mesopores are arranged in a honeycomb pattern.

Glucose Dehydrogenase

The activity of glucose dehydrogenase (GDH) is not influenced by the oxygen concentration, compared with the activity of glucose oxidase. Therefore, a sensor using glucose dehydrogenase is more precise than the one using glucose oxidase when the measurement is carried out in the presence of oxygen. Hence, the use of glucose dehydrogenase is advantageous.

Preferable examples of glucose dehydrogenase include pyrroloquinoline quinone-dependent glucose dehydrogenase (PQQ-GDH, 14 nm), NAD-dependent glucose dehydrogenase (NAD-GDH, 12 nm), and NADP-dependent glucose dehydrogenase (NADP-GDH). In addition, FAD-dependent glucose dehydrogenase may be used.

PQQ-GDH is more stable than NAD-GDH and NADP-GDH and is not readily inactivated even if a clinical diagnostic reagent is added thereto. However, PQQ-GDH also reacts with sugars, such as maltose and galactose. Therefore, in order to achieve higher specificity, NAD-GDH and NADP-GDH are preferable.

The activities of NAD-GDH and NADP-GDH for an oxidation-reduction reaction are low. Therefore, when NAD-GDH or NADP-GDH is used, an electron transfer material (or mediator) may be used. The electron transfer material is reduced when an oxidoreductase oxidizes reduced NAD, and the resulting reduced electron transfer material is oxidized on an electrode by an applied voltage to generate an anode current. This anode current is measured by a sensor. Examples of the electron transfer material include ferricyanide, pyrroloquinoline quinone, 2,6-dichlorophenol indophenol, tetrazolium salts, and ferrocene.

Shape, Pore Size, Length, and Arrangement of Mesopores

Here, mesopores are defined as pores having a pore size of 2 to 50 nm and are defined in the International Union of Pure and Applied Chemistry (IUPAC).

Mesopores in the present invention may have a shape such that the pore size continuously increases from one opening to the other opening or is discontinuously changed. In addition, the mesopores themselves are branched pores.

In the present invention, the mesopores may be arranged at intersections of rows and columns, may be arranged in a honeycomb pattern, or may be regularly or irregularly arranged.

Glucose dehydrogenase, which cannot be immobilized on a porous material with conventional mesopores, can be immobilized on a porous material according to the present invention, because the pore size of the porous material according to the present invention is preferably in the range of about 10 to about 50 nm.

The preferable pore size of the mesopores according to the present invention depends on the intended use of the porous material. For example, when the porous material is for a biosensor, the pore size is preferably 30 nm or less from the viewpoint of stabilizing the conformation of a biological substance. The term "pore size" as used herein refers to a diameter when the cross-section of the pore is a circle and refers to the longest linear cross-sectional dimension of non-circular cross-section, such as a deformed circle or an ellipse.

The mesopores are preferably from about 50 to about 500 nm long. From the viewpoint of being used as a reaction medium in a biosensor, the length is preferably in the range of 50 to 300 nm. With regard to the relationship between the length and pore size of a mesopore, the length of the mesopore may be preferably 30 times or less the pore size. This is because an area of a mesopore that cannot be used as a reaction medium increases with the length of the mesopore. In addition, the distance between adjacent mesopores may be preferably in the range of about 1 to about 4 nm. Furthermore, a plurality of adjacent mesopores may preferably extend in the same direction.

The method for measuring the pore size of mesopores is specifically described below.

Information on pore sizes can be obtained by nitrogen gas adsorption-desorption analysis of a powdered porous material containing mesopores. Specifically, a pore size distribution is calculated from the result of nitrogen gas adsorption analysis by the Berrett-Joyner-Halenda (BJH) method. The pore size distribution of a porous material that is preferably used in the present invention has a single maximum value, and more than 60% of the total number of the mesopores has pore sizes within the distribution range having a width of 10 nm and including the maximum value. According to the Examples described below, more than 90% of the pores may be preferably contained in the 10 nm distribution range.

Information on periodicity of the mesopores can be obtained by X-ray diffraction (XRD) analysis. In the XRD analysis of a structure according to this embodiment, at least one diffraction peak is observed in an angle region equivalent to a structural periodicity of 1 nm or more. This means that the mesopores are regularly arranged.

Manufacturing of Porous Material

A method for manufacturing a porous material containing mesopores according to an embodiment of the present invention is described below.

A reaction solution containing an orientation-controlling agent, a surface-active agent, and a material forming a skeleton of a structure is prepared.

Then, the reaction solution is heated to 100° C. or 120° C. in the presence of a hydrolysis catalyst. Thus, a structure containing the surface-active agent is produced under the conditions for hydrothermal synthesis. As described in the Examples below, rod-shaped particles are produced by the heat treatment at 100° C. and dendritic particles are produced by the heat treatment at 120° C.

Then, the surface-active agent is removed from the structure.

Specifically, a hydrolysis catalyst is added to a reaction solution containing a material forming a skeleton, a surface-active agent, and an orientation-controlling agent. After stirring at about room temperature, the polycondensation reaction of those raw materials is performed, for example, for in the range of several hours to several days. Then, a precipitate generated in the solution is collected, washed, and then dried. Furthermore, the surface-active agent is removed from the precipitate. Thus, a structure containing mesopores passing through the skeleton in a direction crossing the longitudinal axis thereof is obtained.

Examples of the material for forming the skeleton include halides, chalcogenides, and metal alkoxides. When the pore walls of the mesopores are formed of silicon oxide, tetraethoxysilane or tetramethoxysilane, which are metal alkoxides, are preferably used.

With respect to the surface-active agent, nonionic surface-active agents such as block copolymers containing polyethylene oxide as a hydrophilic group are preferably used.

With respect to the orientation-controlling agent, organic substances that can orient a surface-active agent in a direction crossing or intersecting the longitudinal axis of the dendritic skeleton may be used. n-Decane ($C_{10}H_{22}$) is such a substance. The reaction is performed for several hours to several days, and the reaction temperature is adjusted to 100° C. or 120° C. These are atmospheric temperatures in a furnace for heating the solution. The solution is placed in a pressure-resistant container, so that the temperature of the solution is substantially the same as that of the atmosphere.

The obtained porous material precipitates in the solution. Therefore, the porous material can be collected by centrifugation. The collected precipitate is dried using air or the like. The surface-active agent forming a micelle is removed from the collected precipitate to obtain a porous material.

The method for removing the surface-active agent is not specifically limited, as long as the method allows removal of the surface-active agent without destroying the pore structure. For example, the surface-active agent may be removed by being dissolved in a solvent, by extracting the surface-active agent by applying a fluid in a supercritical state into the pores, or by oxidizing the surface-active agent with ozone.

The surface-active agent may be preferably removed by burning the porous material in an atmosphere containing oxygen. For example, the surface-active agent can be removed without actually destroying the mesoporous structure by burning the porous material at 550° C. for 5 hours in air. The burning temperature and time are appropriately determined depending on the materials forming the pore walls or the skeletons and the used surface-active agent that is used.

In addition, a glucose dehydrogenase-immobilizing carrier can be prepared by subjecting the porous material obtained by the above-mentioned method to the following process.

Specifically, the porous material containing mesopores is added into a solution containing glucose dehydrogenase. The glucose dehydrogenase is adsorbed on the pores of the porous material by stirring the solution. In addition, a functional group (for example, an amino group or a carboxyl group) may be introduced onto the pore surface (pore wall surface) of the mesopores so that glucose dehydrogenase is readily adsorbed on the mesopores. It is thought that the electrostatic interaction between the functional group on the pore wall surface and glucose dehydrogenase allows the glucose dehydrogenase to enter the mesopores.

For example, the pore wall surface is modified with a silane coupling agent or is modified by using a metal salt aqueous solution containing a metal that can form an oxide. The silane coupling agent is a compound generally represented by a chemical formula of R—Si—$X_3$ and has at least two different functional groups in its molecule. The X denotes a portion that can react with the pore surface formed of an inorganic substance. For example, in Sol-Gel Science 1989, 662, silicon oxide is used as a mesoporous material. Specifically, hydrogen of a silanol group present on a pore surface is substituted by an organic silicon group to form a Si—O—Si—R bond. Thus, a layer of an organic group R is formed on the pore surface. Examples of groups denoted by X include a chloro group, an alkoxy group, an acetoxy group, an isopropenoxy group, and an amino group. The group denoted by X may be not only trifunctional, but can also be bifunctional or monofunctional, as long as the coupling agent can react with a pore surface and form a layer of a group denoted by R. R represents an organic group such as an amino group, a carboxyl group, or a maleimide group.

In addition, when the pore surface is modified with a metal salt aqueous solution containing an element that can form an oxide, the element that can form an oxide layer may be titanium, aluminum, zirconium, or tin. For example, a layer of zirconium oxide can be formed on a pore surface by treating mesoporous silica with a zirconium oxynitrate aqueous solution.

Each mesopore can receive at least one glucose dehydrogenase. Therefore, the mesopore must have a size suitable for immobilizing glucose dehydrogenase.

When the sizes of a mesopore and glucose dehydrogenase are compatible, glucose dehydrogenase can approach the pore wall of the mesopore. Then, glucose dehydrogenase is adsorbed on the mesopore walls by Van der Waals forces. Hence, the conformation of glucose dehydrogenase can be retained and the inactivation of glucose dehydrogenase can be avoided. In addition to the immobilization utilizing Van der Waals interactions, glucose dehydrogenase may be immobilized on mesopore walls by a noncovalent bond, i.e., an electrostatic bond, a hydrogen bond, or an ionic bond.

Furthermore, novel findings related to a method for immobilizing glucose dehydrogenase on mesopores have been obtained. Conventionally, it has been thought that a larger amount of a biological substance can be immobilized on a carrier when a difference between the electric charges of the biological substance and the carrier surface is also large, because a stronger electrostatic adsorption is achieved due to the large difference. However, it has been confirmed that electrically charged NAD-GDH is not readily introduced into the mesopores due to electrostatic repulsion. Thus, the amount of the immobilized NAD-GDH is limited. Accordingly, in the present invention, the electrostatic repulsion between NAD-GDH molecules is reduced by increasing the salt concentration of a buffer solution to increase the ionic strength of a NAD-GDH aqueous solution. However, if the electrostatic repulsion is zero, GDH molecules agglutinate. Consequently, the solution is prepared so that it is slightly charged. It has been confirmed that the amount of NAD-GDH immobilized on the pore walls can be controlled by controlling the salt concentration of the buffer solution by this method and that the maximum amount of immobilized NAD-GDH can be significantly increased compared to that achieved by a conventional method.

Functional Device Using Porous Material According to the Present Invention

As described above, a porous material containing mesopores with immobilized glucose dehydrogenase can be used in a biosensor as a functional device.

A method for detecting an analyte according to an embodiment of the present invention is described below.

First, a sensor provided with the above-mentioned porous material containing mesopores immobilized with glucose dehydrogenase is prepared. Then, a fluid (liquid or gas) containing an analyte is applied to the sensor. The fluid containing the analyte penetrates into the mesopores, and the analyte reacts with glucose dehydrogenase immobilized on the mesopore walls. Then, the output signal based on the reaction between the glucose dehydrogenase and the analyte is detected.

A target analyte is determined on the basis of a principle that a specific binding reaction of an analyte causes a change in quantity of a physical parameter, such as current, pressure, mass, or heat.

The structure according to the present invention can also be used not only as a biosensor functional device, but also as a column, such as an absorbent or a separating agent. In that case, a large amount of particles composed of the porous material of the above-mentioned embodiment are prepared and these particles may be molded into a porous material.

Then, by providing an electrode to a combination of this porous material and an electron transfer material, a change in the above-mentioned physical quantity can be detected as an electrical output signal.

Example 1

Immobilization of PQQ-Glucose Dehydrogenase on Mesopores of Rod-Shaped Particles In this Example, mesoporous silica containing tube-shaped mesopores intersecting the longitudinal axis direction of the rod is prepared. A method for manufacturing a structure containing tube-shaped mesopores immobilized with PQQ-GDH (pyrroloquinoline-dependent glucose dehydrogenase) is described below.

Method for Manufacturing Rod-Shaped Porous Material

A triblock copolymer ($EO_{20}PO_{70}EO_{20}$; $HO(CH_2CH_2O)_{20}(CH_2CH(CH_3)O)_{70}(CH_2CH_2O)_{20}H$) (2.40 g), as a nonionic surface-active agent, was dissolved in 76.5 ml of pure water. After the addition of 7.5 ml of 36 wt % concentrated hydrochloric acid, the mixture solution was stirred at room temperature for 30 minutes. Then, 13.9 g of n-decane was added to the solution and the resulting mixture solution was stirred at room temperature for 2 hours.

Then, 0.027 g of $NH_4F$, as a hydrolysis catalyst, and 5.10 g of tetraethoxysilane (TEOS) were added to this mixture solution to prepare a preliminary solution. The final composition (molar ratio) of the preliminary solution was adjusted to TEOS:HCl:$EO_{20}PO_{70}EO_{20}$:$NH_4F$:n-decane:$H_2O$=0.25:0.9:0.004:0.007:1:42.9.

The preliminary solution was stirred at 40° C. for 20 hours and was then left for the reaction at 100° C. for 48 hours. The resulting white precipitate was sufficiently washed with pure water and vacuum-dried.

The resulting powder was burned at 550° C. in air to decompose and remove the surface-active agent from the mesopores. Thus, hollow mesopores were prepared. The removal of organic substances such as the surface-active agent was confirmed by an infrared absorption spectrum.

Figure 3:
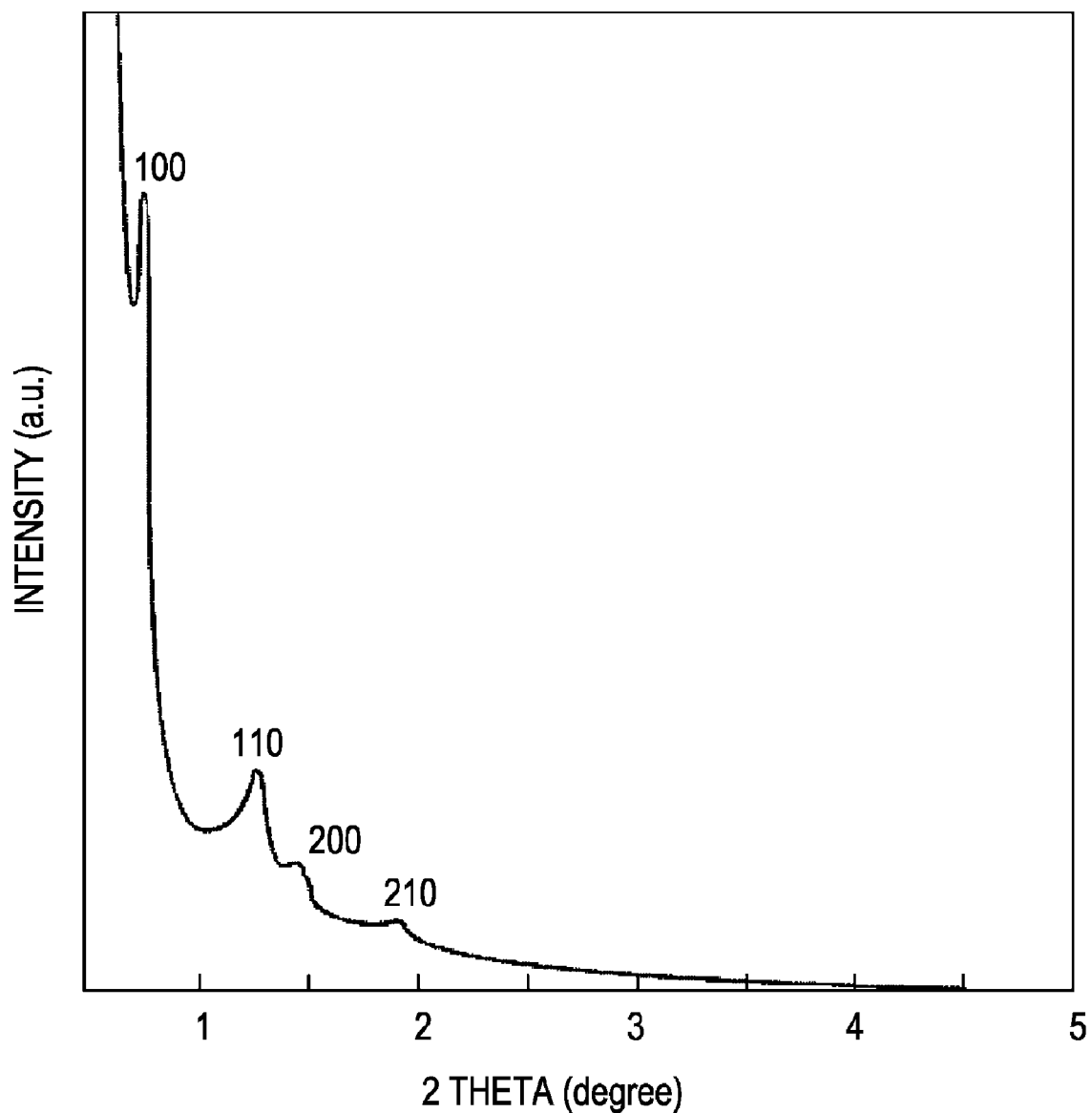
FIG. 3 is a graph showing a result of X-ray diffraction analysis.

The synthesized mesoporous silica powder was evaluated by X-ray diffraction analysis. FIG. 3 shows the result. A major diffraction peak assigned to the (100) plane of a hexagonal structure having an interplanar spacing of 11.7 nm was confirmed. In addition, diffraction peaks assigned to the (110), (200), and (210) planes were confirmed. This result shows that the mesoporous structure of the mesoporous silica has a highly regular hexagonal arrangement.

The nitrogen adsorption-desorption isotherm at 77 K was measured. The results showed that the adsorption isotherm was a type IV isotherm according to the IUPAC classification. The specific surface area calculated by the BET method was 700 $m^2$/g, and the mesopore capacity was 1.88 ml/g. The mesopore sizes were calculated on the basis of the result of the adsorption isotherm by the BJH method. The mesopore size distribution of the mesoporous silica synthesized in this Example had a narrow distribution with a single peak at 14.1 nm, and more than 90% of the total number of the mesopores has pore sizes within the distribution range having a width of 10 nm.

Figure 4:
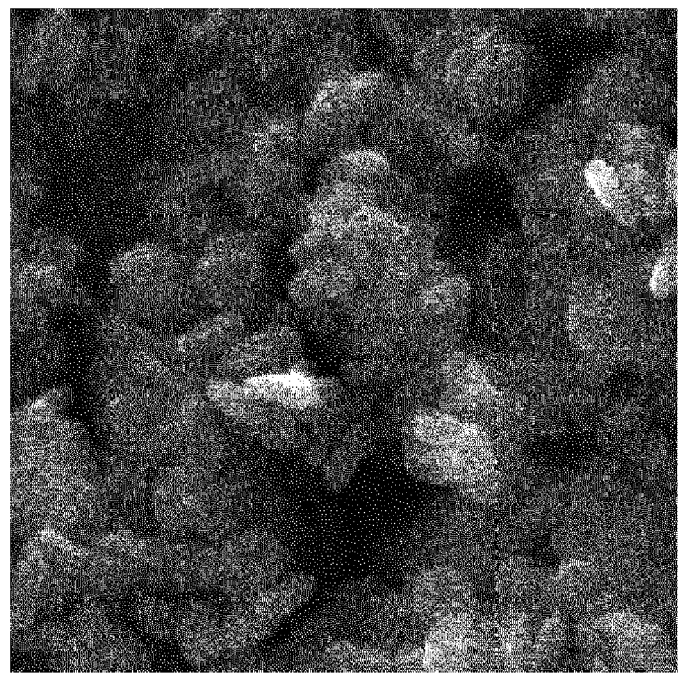
FIG. 4 is a scanning electron microscope photograph of rod-shaped particles.
Figure 5:
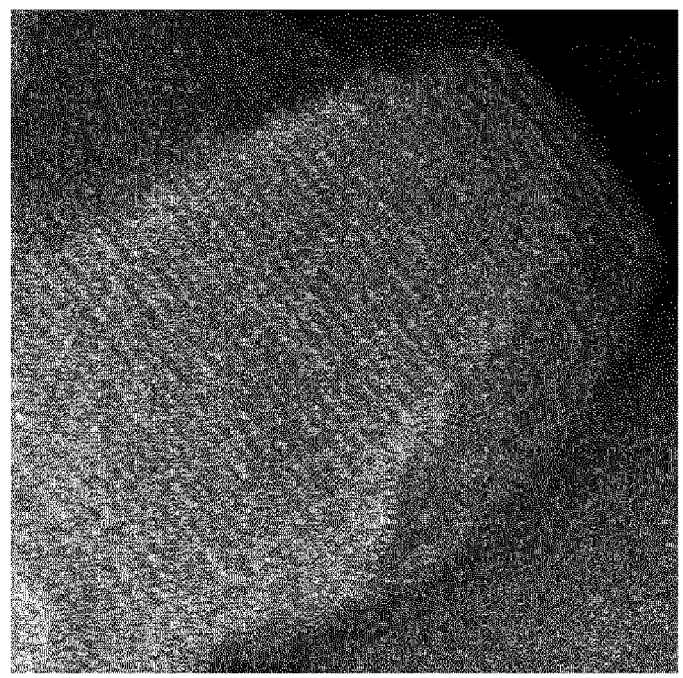
FIG. 5 is a scanning electron microscope photograph of rod-shaped particles.
Figure 6:
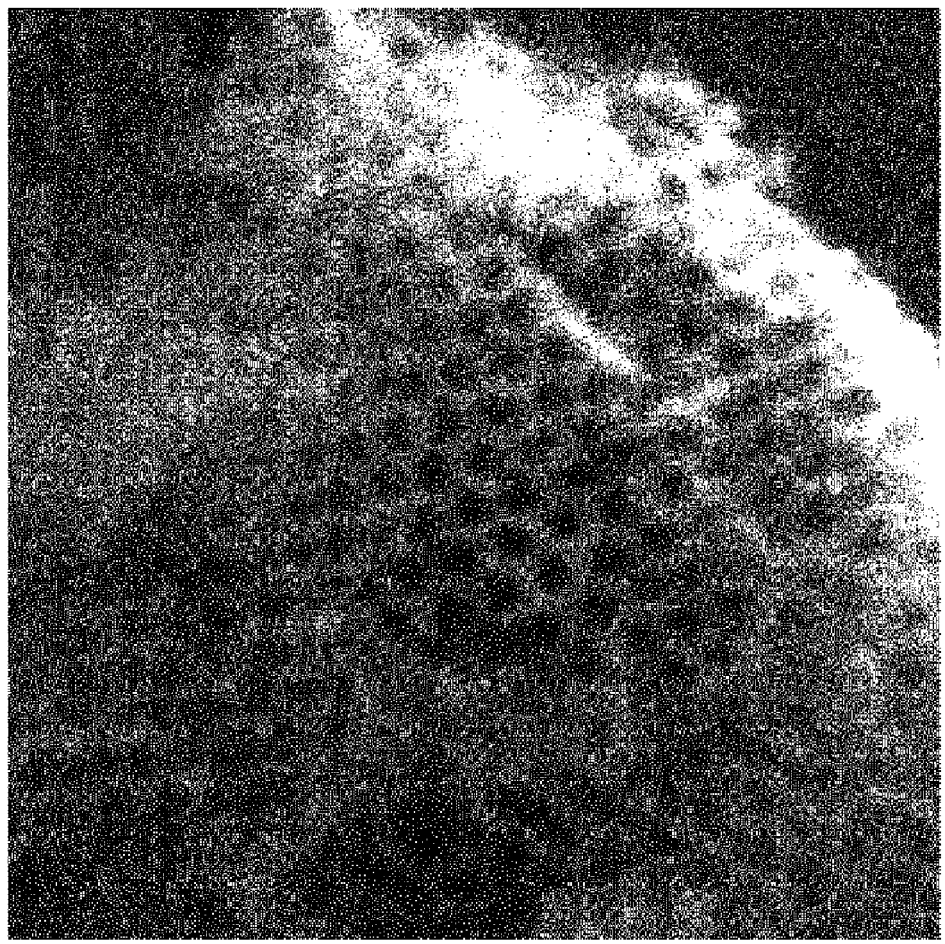
FIG. 6 is a scanning electron microscope photograph of rod-shaped particles.

Next, the observation was carried out using a scanning electron microscope (SEM). As shown in FIG. 4, a rod-shaped structure was observed. Further observation at a higher magnification with the SEM confirmed that, as shown in FIG. 5, the tube-shaped mesopores with a diameter of 14 nm were oriented in the minor axis direction of the structure. The cross-sections are shown in FIG. 6.

Relatively uniform tube-type mesopores formed a pore structure resembling a honeycomb. In addition, no damage to the mesopore structure due to the electron beams occurred during the observation.

Immobilization of GDH on Mesopores

Then, PQQ-GDH is adsorbed on the mesopore walls of the mesoporous silica and the thermal stability is measured.

A 5 mg/ml PQQ-GDH aqueous solution was prepared by using a 20 mM 3-morpholinopropane sulfonic acid (MOPS) buffer solution (pH 7.0). To 1 ml of this PQQ-GDH aqueous solution, 5 mg of the mesoporous silica synthesized by the above-mentioned method was added. The mixture solution was stirred with a shaker for 20 hours at 4° C. to adsorb the PQQ-GDH on the mesopore walls of the mesoporous silica. After the stirring, the mixture solution was centrifuged at 20000 g for 10 minutes at 4° C. to obtain PQQ-GDH-immobilizing silica. The amount of PQQ-GDH immobilized on the mesoporous silica was calculated by using the absorption maxima at 280 nm of supernatants at 280 nm before and after the PQQ-GDH adsorption. The amount of the adsorbed PQQ-GDH was about 230 mg/g. The fact that the PQQ-GDH molecules were not adsorbed to the external surface of the mesoporous silica but adsorbed on the mesopore walls was confirmed by measuring a change in the adsorption behavior with respect to the mesopore walls before and after the adsorption of PQQ-GDH to the mesoporous silica with a nitrogen adsorption measurement device.

Thermal Properties of Rod-Shaped Particles Immobilized with PQQ-GDH

To 5 mg of the PQQ-GDH-immobilizing mesoporous silica prepared by the above-described PQQ-GDH adsorption, 1 ml of 10 mM MOPS buffer solution (pH 7.0) was added. The mixture solution was heated at 70° C. for 30, 60, 90, or 120 minutes. After the heating, the mixture solution was centrifuged to obtain PQQ-GDH-immobilizing silica. The PQQ-GDH-immobilizing silica was washed twice with pure water. To the PQQ-GDH-immobilizing silica, 500 µl of 5 mM MOPS buffer solution (pH 7.0), 100 µl of 20 mM phenazine methosulfate (PMS), 100 µl of 4 mM 2,6-dichloroindophenol (DCIP), and 300 µl of 1.2 M glucose aqueous solution were added, and the mixture solution was subjected to a reaction at 25° C. for 3 minutes. After centrifugation, the supernatant was rapidly collected and the absorbance of the supernatant at about 600 nm was measured.

As a comparative test, 0.5 mg of PQQ-GDH alone was heated as described above and was subjected to an oxidation reaction, and the absorbance at about 600 nm was similarly measured.

Figure 7:
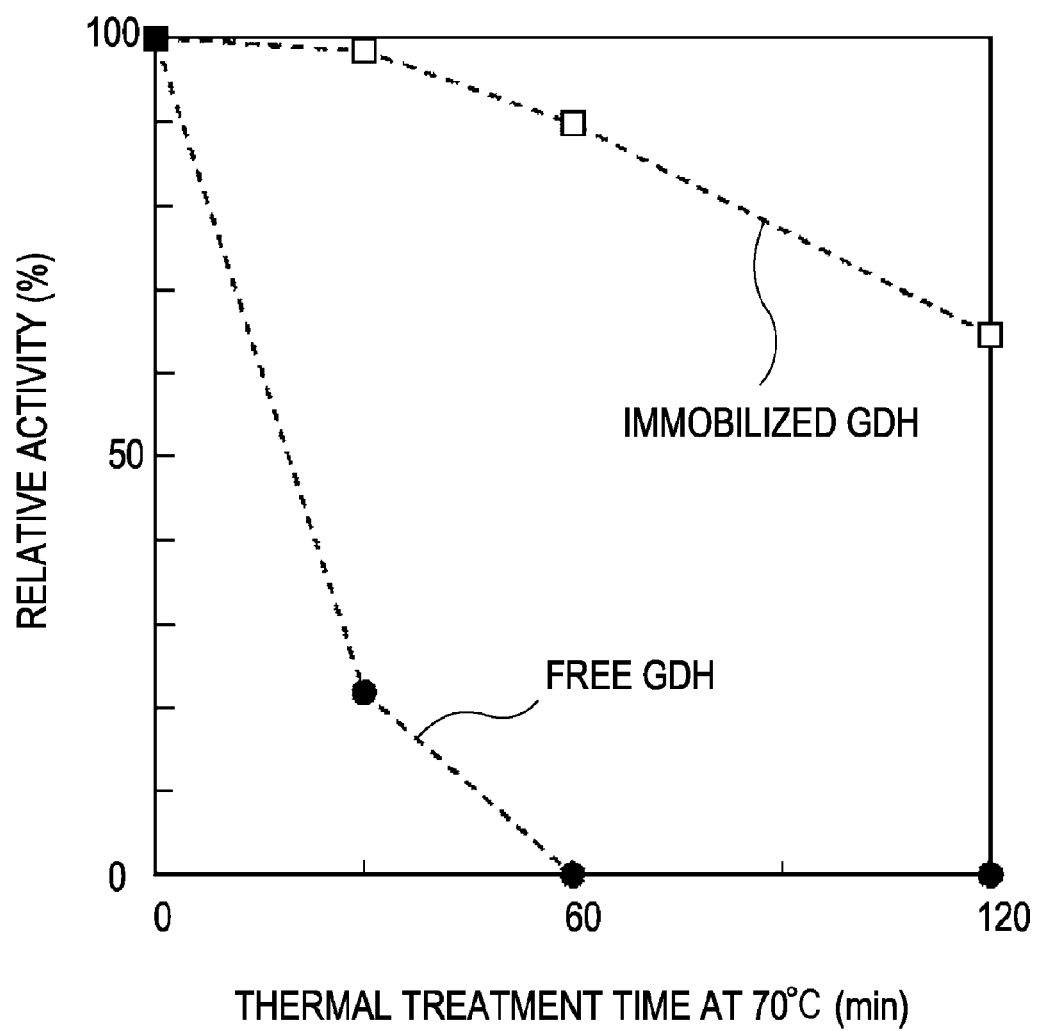
FIG. 7 is a graph showing the relationship between temperature and enzyme activity.

FIG. 7 shows the changes in the relative activity in a case of a heat treatment conducted at 70° C. Free PQQ-GDH (simply dispersed in a buffer solution) that was not immobilized on silica was completely inactivated by heating at 70° C. for 60 minutes. However, PQQ-GDH immobilized on the synthesized mesoporous silica was confirmed to be highly resistant to heat.

Figure 8:
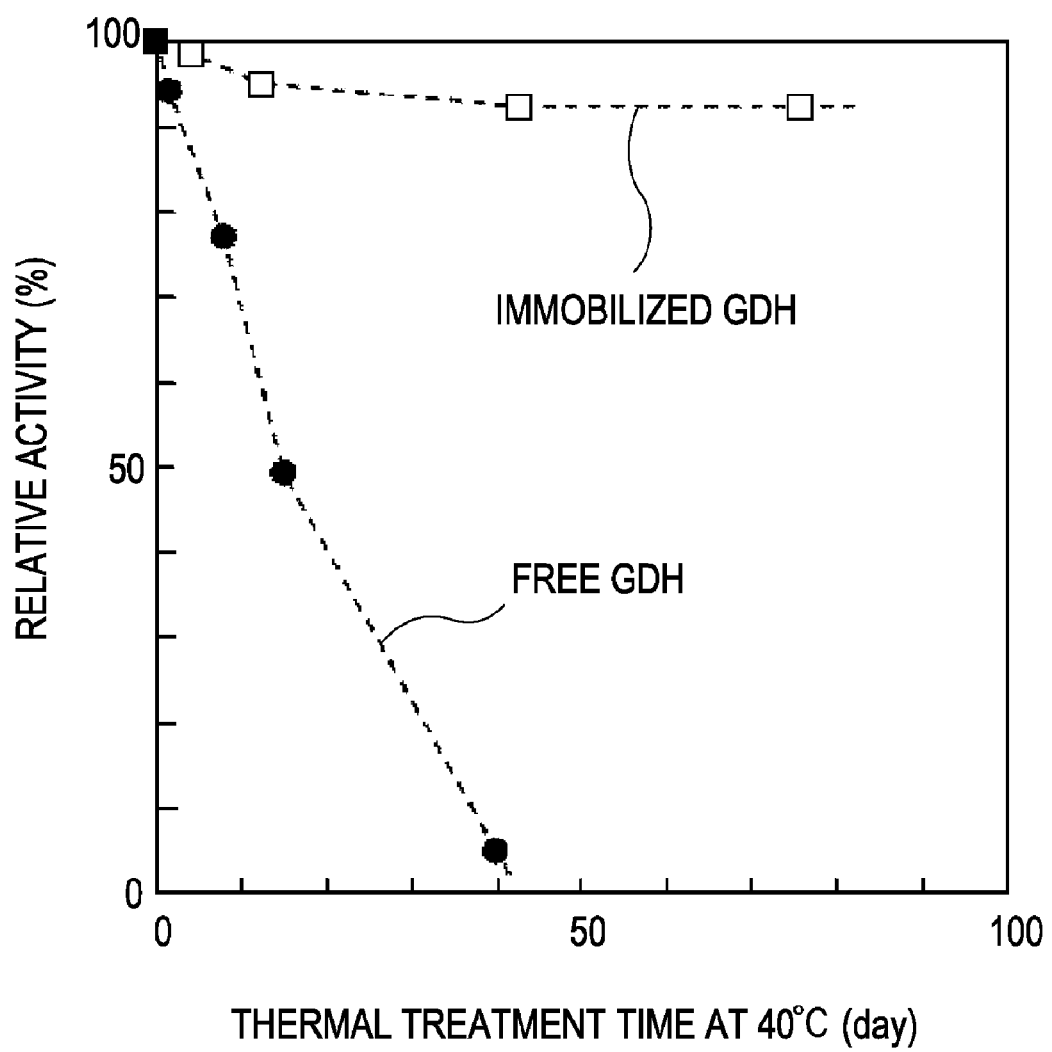
FIG. 8 is a graph showing the relationship between temperature and enzyme activity.

FIG. 8 shows the results of the heat stability analysis in a case of a heat treatment conducted at 40° C. The PQQ-GDH-immobilizing mesoporous silica (5 mg) prepared by the above-mentioned PQQ-GDH adsorption was vacuum-dried. The dried mesoporous silica was left in a constant-temperature box at 40° C. for a predetermined time. Lyophilized free PQQ-GDH was left under the same conditions as above. Then, to the PQQ-GDH-immobilizing mesoporous silica or the free PQQ-GDH, 500 µl of 10 mM MOPS buffer solution (pH 7.0), 100 µl of 20 mM PMS, 100 µl of 4 mM DCIP, and 300 µl of 1.2 M glucose aqueous solution were added. The PQQ-GDH immobilized on the silica and the free PQQ-GDH were subjected to a reaction at 25° C. for 3 minutes. After centrifugation, the supernatants were rapidly collected and the absorbance of each supernatant at about 600 nm was measured. The free PQQ-GDH that was not immobilized on mesoporous silica was approximately completely inactivated by heating at 40° C. for about 40 days. The reactive activity is near 0. However, the PQQ-GDH immobilized on the mesoporous silica retained more than 90% of the activity after 100 days.

As described above, it has been confirmed that the stability of PQQ-GDH can be significantly improved by immobilizing PQQ-GDH on mesopore walls. Therefore, the present invention can provide a biosensor that can be driven more stably than known biosensors under high temperature conditions.

Example 2

Immobilization of PQQ-glucose Dehydrogenase on Mesopores of Dendritic Particles In this Example, a porous material containing macropores consisting of three-dimensionally formed gaps by branched rod-shaped skeletons and mesopores is prepared. A structure containing mesopores with immobilized PQQ-GDH and a method for manufacturing the structure is described below.

Manufacturing of Dendritic Particles

Figure 9:
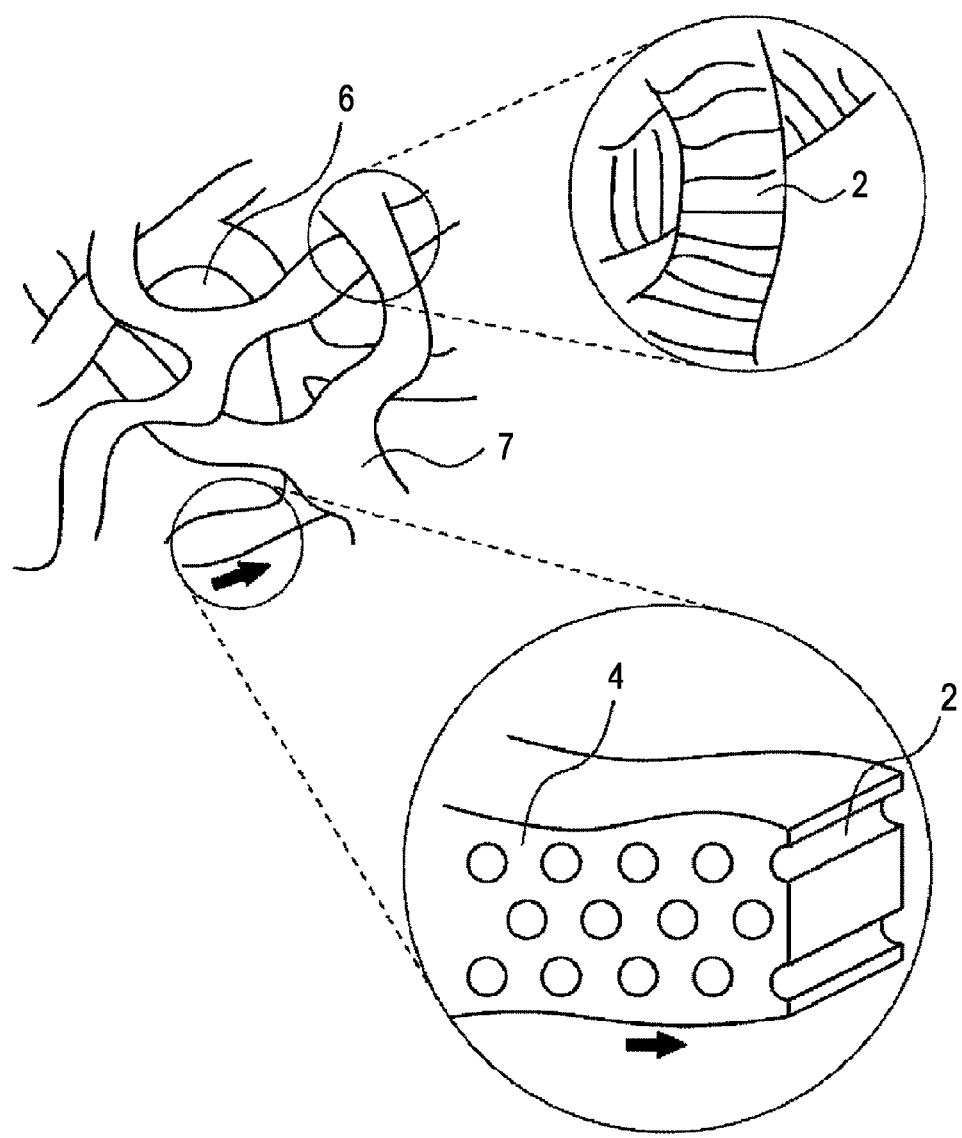
FIG. 9 is a schematic diagram illustrating a dendritic particle according to an embodiment of the present invention.
Figure 10:
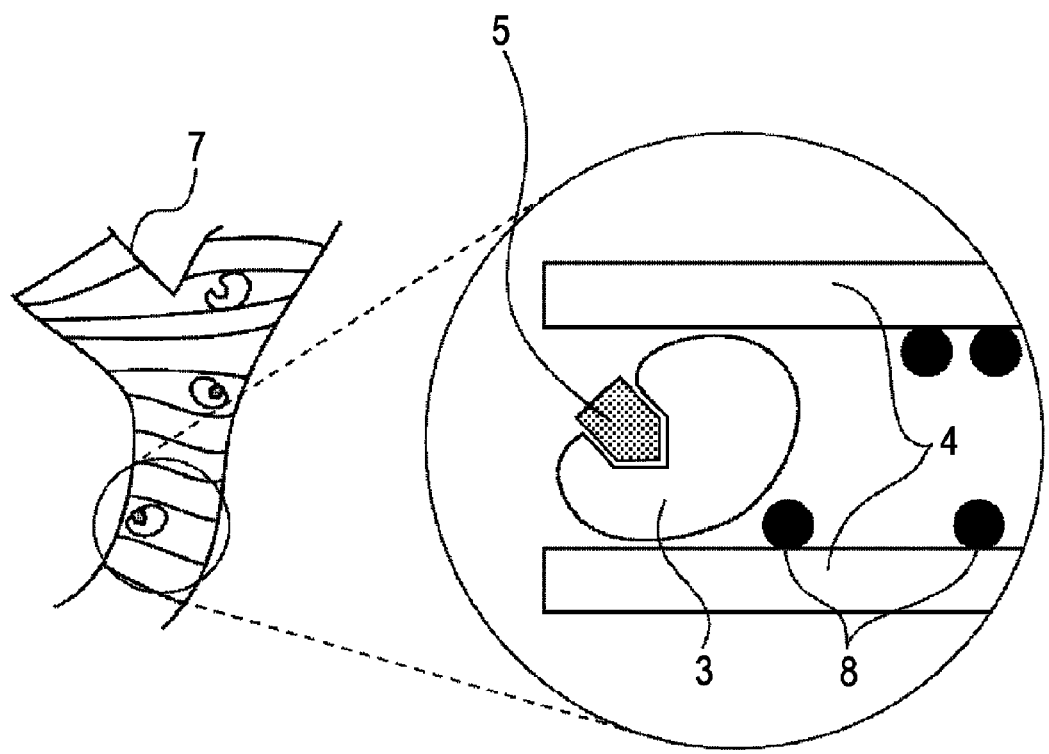
FIG. 10 is a schematic diagram illustrating a dendritic particle according to an embodiment of the present invention.

First, the form of dendritic particles will be described by referring to FIGS. 9 and 10. The dendritic skeleton 7 has a complicated structure. Gaps formed between adjacent skeleton branches and having macropore sizes are defined as macropores 6. The size of the macropores 6 is at least 50 nm, and preferably 100 to 700 nm in the present invention. The skeleton 7 is provided with mesopores 2 that are tube-shaped so as to cross the longitudinal axis direction indicated by the arrow. The dendritic particle is further enlarged as shown in FIG. 10 to observe glucose dehydrogenase 3 immobilized in the mesopore 2. FIG. 10 is a schematic diagram illustrating a reaction between glucose 5 and glucose dehydrogenase 3. In addition, electrical information from glucose and glucose dehydrogenase can be more readily obtained by using an electron transfer material 8, and the application in a biosensor is further expected. An anodic oxidation current based on the transfer of electrons on an electrode is detected as an electrical signal.

A manufacturing method will now be specifically described.

A triblock copolymer ($EO_{20}PO_{70}EO_{20}$; $HO(CH_2CH_2O)_{20}(CH_2CH(CH_3)O)_{70}(CH_2CH_2O)_{20}H$) (2.40 g), as a nonionic surface-active agent, was dissolved in 76.5 ml of pure water. After the addition of 7.5 ml of 36 wt % concentrated hydrochloric acid, the mixture solution was stirred at room temperature for 30 minutes. Then, 13.9 g of n-decane was added to the solution and the resulting mixture solution was stirred at room temperature for 2 hours. Then, 0.027 g of $NH_4F$, as a hydrolysis catalyst, and 5.10 g of tetraethoxysilane (TEOS) were added to this mixture solution to prepare a preliminary solution. The final composition (molar ratio) of the preliminary solution was adjusted to TEOS:HCl:$EO_{20}PO_{70}EO_{20}$:$NH_4F$:n-decane:$H_2O$=0.25:0.9:0.004:0.007:1:42.9.

The preliminary solution was stirred at 40° C. for 20 hours and was subjected to a reaction at 120° C. for 48 hours. The resulting white precipitate was sufficiently washed with pure water and was vacuum-dried.

The resulting powder precipitate was burned at 550° C. in air to decompose and remove the surface-active agent from mesopores. The removal of organic substances, such as the surface-active agent, was confirmed by an infrared absorption spectrum.

X-ray diffraction analysis, nitrogen adsorption-desorption isotherm measurement, and scanning electron microscope (SEM) observation were carried out as in Example 1.

The result of the X-ray diffraction analysis, like the result shown in FIG. 3, confirmed a major diffraction peak assigned to the (100) plane of a hexagonal structure having an interplanar spacing of 11.7 nm. In addition, diffraction peaks assigned to the (110), (200), and (210) planes were confirmed. This shows that the mesoporous structure of the mesoporous silica has a highly regular hexagonal arrangement.

The result of the nitrogen adsorption-desorption isotherm measurement showed that the adsorption isotherm was a type IV isotherm according to the IUPAC classification. The specific surface area calculated by the BET method was 700 $m^2$/g, and the mesopore capacity was 1.88 ml/g. The mesopore sizes were calculated by the BJH method on the basis of the result of the adsorption isotherm. The mesopore size distribution of the mesoporous silica synthesized in this Example had a narrow distribution with a single peak at 14.1 nm, and more than 90% of the total number of the mesopores has pore sizes within the 10 nm width distribution range.

Figure 11:
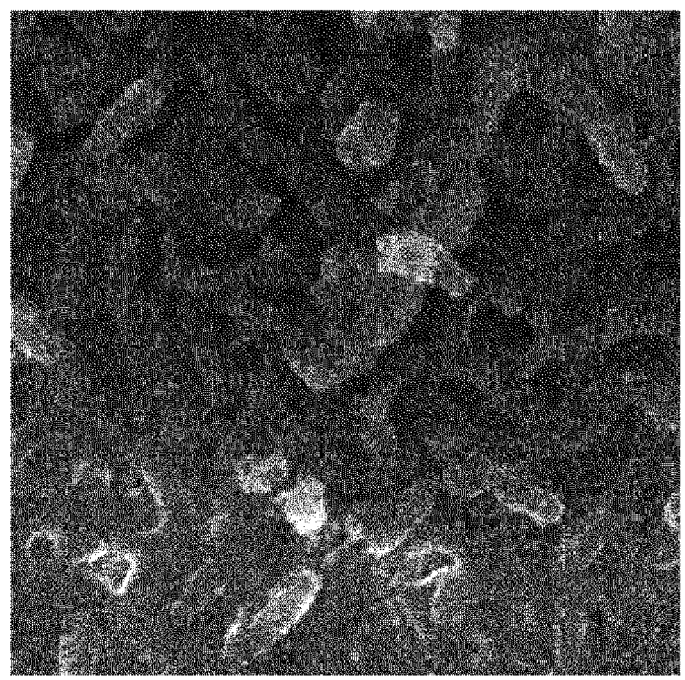
FIG. 11 is a scanning electron microscope photograph of dendritic particles.
Figure 12:
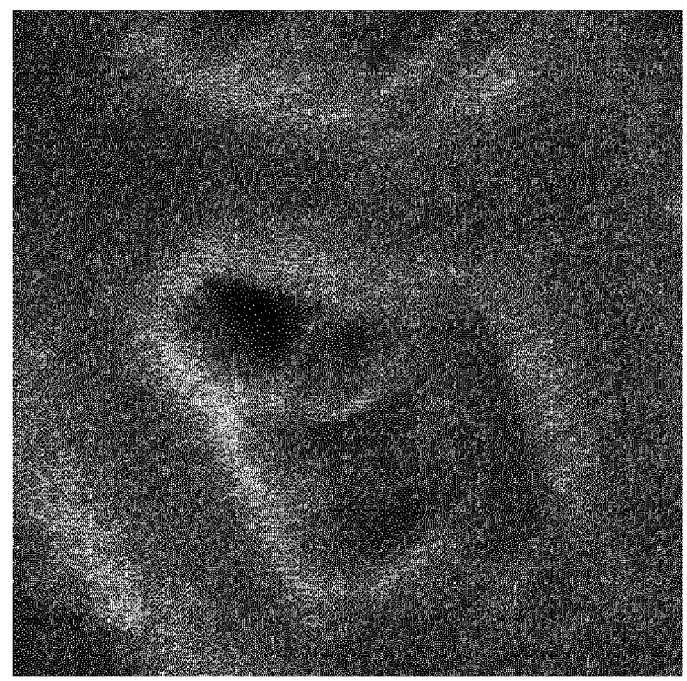
FIG. 12 is a scanning electron microscope photograph of dendritic particles.

The observation was carried out using a scanning electron microscope (SEM). As shown in FIG. 11, a dendritic-shaped structure was observed. Further observation at a higher magnification with the SEM confirmed that, as shown in FIG. 12, tube-shaped mesopores with a diameter of 14 nm were oriented in the minor axis direction of the structure. In addition, no damage to the mesopore structure due to the electron beams occurred during the observation.

These results confirmed that dendritic particles containing macropores and mesopores were obtained.

Since these particles contain hierarchically formed macropores and mesopores, the particles are also referred to herein as hierarchical particles.

Immobilization of GDH on Mesopore Walls (1) Without Surface Modification

PQQ-GDH was immobilized on the mesopore walls of the dendritic particles by the same method as that used in Example 1. The fact that the PQQ-GDH was immobilized on the mesopore walls was confirmed with a nitrogen adsorption measurement device as in Example 1, namely, by using a change in the adsorption behavior with respect to the mesopores before and after the adsorption of PQQ-GDH to the mesoporous silica.

Immobilization of GDH on Mesopore Walls (2) with Surface Modification

The synthesized hierarchical mesoporous silica (1.0 g) was added to 50 ml of a 5% (v/v) 3-aminopropyl triethoxysilane toluene solution. This solution was stirred under nitrogen atmosphere at 120° C. for 48 hours. After the reaction, the precipitate was filtered and washed with toluene, ethanol, and dichloromethane, and then vacuum-dried.

Then, 1.0 g of the dried precipitate was dissolved in 25 ml of a 2.5% glutaraldehyde phosphate buffer solution (pH 6.6). The solution was stirred at room temperature for 1 hour. The resulting precipitate was washed with pure water four times or more and was then dried at room temperature.

The hierarchical mesoporous silica modified with glutaraldehyde was evaluated by powder X-ray diffraction analysis. The resulting diffraction pattern was approximately the same as that before the modification. Thus, it was confirmed that the mesoporous structure was not damaged due to surface modification. In addition, functional groups introduced to the silica surface were identified by using Fourier-transform infrared (FT-IR) spectroscopy, and peaks caused by R—CH=N, C=O, and —CHO and $Si(CH_2)_3NH=CH(CH_2)_3CHO$ covalently bonded to the silica surface were confirmed.

Then, PQQ-GDH was immobilized on mesopore walls of the modified hierarchical mesoporous silica.

A 5 mg/ml PQQ-GDH solution was prepared by using a 20 mM MOPS buffer solution (pH 7.0). To 1 ml of this PQQ-GDH solution, 10 mg of the hierarchical mesoporous silica synthesized and modified by the above-mentioned method was added. This mixture solution was stirred with a shaker at 4° C. for 20 hours so that the PQQ-GDH was adsorbed on the mesoporous walls of the mesoporous silica. After the reaction, the solution was filtered, and the silica was washed with pure water three times. The original PQQ-GDH solution and the supernatant in this case were subjected to a UV-Vis absorbance measurement. The amount of PQQ-GDH adsorbed on the mesoporous silica was calculated from the change in the concentrations of PQQ-GDH before and after the adsorption by using the absorption maxima of PQQ-GDH at 280 nm. The amount of the adsorbed PQQ-GDH was 150 mg/g.

Then, in order to confirm desorption behavior of PQQ-GDH from the mesoporous silica, the following experiment was carried out. The dendritic particles in which mesopore walls were modified and PQQ-GDH was immobilized thereon were put into 1 ml of pure water, and the mixture solution was gently shaken at 4° C. The absorbance of the supernatant at 280 nm was measured at regular time intervals. For comparison, dendritic particles immobilized with PQQ-GDH without the modification of the mesopore surfaces were subjected to desorption behavior analysis by the same method as above. In the particles that were immobilized with PQQ-GDH after the modification of the silica surface with an organic substance, almost no desorption of PQQ-GDH was observed after 12 hours from the start of the shaking. On the other hand, in the particles immobilized with PQQ-GDH without the modification of the surface, desorption of PQQ-GDH was observed. The amount of the desorbed PQQ-GDH was 5% or less of the total amount of the adsorbed PQQ-GDH. Therefore, it was suggested that —CHO modifying the silica surface and —NH$_2$ of PQQ-GDH were bound to each other and thereby the PQQ-GDH was covalently immobilized on the silica surface. Consequently, it is suggested that PQQ-GDH can be efficiently immobilized on a surface at a predetermined position by modifying the surface.

Thermal Properties of Dendritic Particles Immobilized with PQQ-GDH

Mesoporous silica with immobilized PQQ-GDH and mesoporous silica with PQQ-GDH that is not immobilized were heated at 70° C. as in Example 1, and the enzyme activities of the PQQ-GDH were measured.

The experiment conditions were the same as those in Example 1, except that hierarchical mesoporous silica was used.

The results showed that the free PQQ-GDH (simply dispersed in a buffer solution) not immobilized on mesoporous silica was completely inactivated by heating at 70° C. for 60 minutes, like the results in Example 1. On the other hand, PQQ-GDH immobilized on the hierarchical mesoporous silica synthesized in this Example was confirmed to have thermal stability.

Example 3

Conditions for Immobilizing PQQ-Glucose Dehydrogenase on Mesopores

In this Example, salt concentration and pH of a buffer solution suitable for efficiently introducing PQQ-GDH to the synthesized mesoporous silica are investigated.

A 5 mg/ml PQQ-GDH solution was prepared by using an MOPS buffer solution (pH 7.0). The salt concentration of each MOPS buffer solution was adjusted to 0.1, 0.5, 1.0, 5.0, 10.0, or 20.0 mM. To 1 ml of each PQQ-GDH solution, 5 mg of the hierarchical mesoporous silica synthesized in Example 2 was added. This mixture solution was stirred with a shaker at 4° C. for 20 hours to adsorb the PQQ-GDH on the mesopore walls of the mesoporous silica. After the stirring, the solution was centrifuged at 20000 g for 10 minutes at 4° C. to prepare PQQ-GDH-immobilizing silica at each salt concentration. The amount of PQQ-GDH adsorbed on the mesoporous silica was calculated by using the absorption maxima of PQQ-GDH of supernatants at 280 nm before and after the adsorption of PQQ-GDH. The fact that the PQQ-GDH molecules in each mixture solution were not adsorbed to the external surface of the mesoporous silica but adsorbed on the mesopore walls was confirmed by measuring a change in the adsorption behavior with respect to the mesopore walls before and after the adsorption of PQQ-GDH to the mesoporous silica with a nitrogen adsorption measurement device.

It was confirmed that the amount of PQQ-GDH adsorbed on the mesopore walls increased in a curve pattern according to an increase in the salt concentration of the buffer solution. When the 20 mM MOPS buffer solution was used, the adsorption amount was a maximum of 240 mg/g. In addition, a 5 mg/ml PQQ-GDH aqueous solution was prepared by dissolving PQQ-GDH in a 0.1 mM MOPS buffer solution so that the pH of the PQQ-GDH aqueous solution is 9.0, which is near the isoelectric point of PQQ-GDH, and a similar adsorption experiment was conducted by using this PQQ-GDH aqueous solution. When the pH was 7.0, the amount of adsorbed PQQ-GDH was 100 mg/ml. When the pH was 9.0, the adsorption amount was 220 mg/ml, which was about twice that at the pH of 7.0.

The above-described results suggest that a reaction system in which electrostatic repulsion is relieved is required for efficiently introducing PQQ-GDH into the mesopores. In addition, the results suggest that such a reaction system may be prepared by any methods, e.g., increasing the salt concentration of a buffer solution or adjusting the pH to about the isoelectric point of PQQ-GDH. Herein, a method for increasing a salt concentration is the method for relieving the electrostatic repulsion between biological substances by increasing the concentration of a buffer solution and thereby increasing ionic strength in the reaction system. The method for introducing PQQ-GDH into mesopores by controlling the salt concentration will be excellent, considering the fact that the optimum pH of PQQ-GDH is about 7.0.

Example 4

Biosensor Using a Structure Containing Mesopores Immobilized with PQQ-GDH

Figure 14:
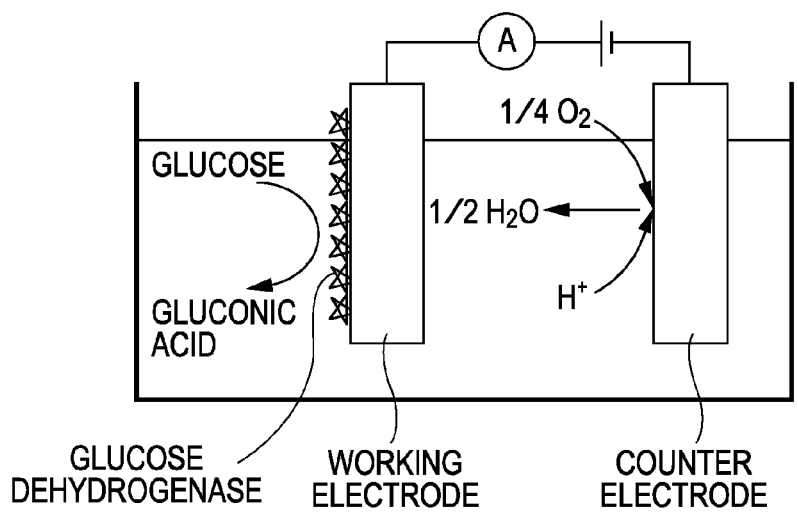
FIG. 14 is a schematic diagram illustrating a glucose sensor.

FIG. 14 illustrates this Example. The hierarchical mesoporous silica synthesized in Example 2 is formed on an electrode. Furthermore, PQQ-dependent glucose dehydrogenase and a mediator are immobilized on mesopore walls. The glucose concentration is measured by the thus prepared device. A carbon electrode (working electrode) and a platinum electrode (counter electrode) are used.

A 5 mg/ml PQQ-GDH solution was prepared by using a 20 mM MOPS buffer solution (pH 7.4). Mesoporous silica synthesized in Example 2 and a carbon electrode were immersed in 10 ml of this enzyme solution. The solution was gently stirred with a shaker at 4° C. for 20 hours to adsorb the PQQ-GDH on mesopore walls of the mesoporous silica on the electrode. After the reaction and centrifugation, the PQQ-GDH-immobilizing mesoporous silica on the electrode was washed with pure water three times to obtain a PQQ-GDH-immobilizing electrode. The amount of PQQ-GDH adsorbed on the mesoporous silica was calculated by using the absorption maxima of the supernatants at 280 nm before and after the immobilization of PQQ-GDH and by subtracting the amount of PQQ-GDH adsorbed on the carbon electrode only as a background. The amount of PQQ-GDH adsorbed on the mesoporous silica was 230 mg/g or more. In addition, a 100 mM potassium ferricyanide solution was prepared by using 50 ml of an MOPS buffer solution. The electrode attached to the mesoporous silica was dried and then immersed in 100 ml of the potassium ferricyanide solution at room temperature for 12 hours in order to immobilize a mediator on the mesopore walls. After the immersion and centrifugation, the electrode with the attached mesoporous silica was washed with pure water and then dried at room temperature to obtain a GDH-immobilizing electrode for measuring glucose.

The measurement of the glucose concentration was carried out as follows. A 50 mM MOPS buffer solution was put in a constant-temperature cell and the temperature was maintained at a constant level. The above-synthesized PQQ-GDH-immobilizing carbon electrode was used as a working electrode, and a platinum electrode was used as a counter electrode. A constant pressure was applied to the carbon electrode. After the current reached a steady state, a specimen containing glucose was applied to the electrode. An increase in the current was measured to confirm that a high value was achieved. In addition, currents of standard glucose solutions were measured to confirm that the current linearly increased with an increase in the glucose concentration.

In order to measure the thermal stability of this electrode, the electrode was heated at 70° C. for 30 minutes in the MOPS solution in a constant-temperature cell, and then, the glucose concentration was similarly measured by using this electrode. The current was approximately the same as that in the above-described experiment. Hence, it was confirmed that PQQ-GDH immobilized on the electrode also had high thermal stability.

Figure 13:
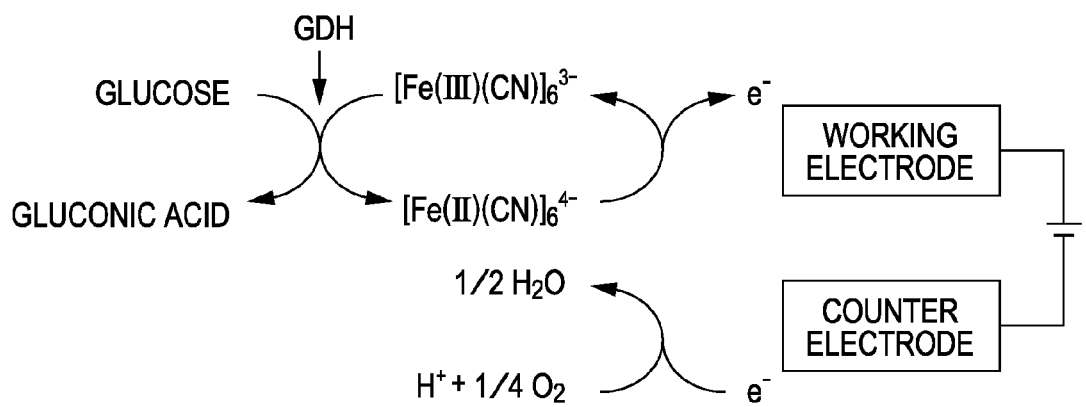
FIG. 13 is a diagram showing a reaction between glucose dehydrogenase and glucose.

The reaction mechanism of PQQ-dependent GDH enzyme is detailed in FIG. 13. D-Glucose as a substrate is oxidized to transfer electrons to pyrroloquinoline quinine coordinated to the enzyme. The electrons are further transferred to ferricyanide ions as a mediator.

Based the above-described results in this Example, it was confirmed that a glucose-measuring reagent composition and a highly stable glucose sensor can be manufactured by using the above-mentioned PQQ-GDH-immobilizing silica and an electron mediator.

Example 5

Conditions for Immobilizing NAD-Glucose Dehydrogenase on Mesopores

Rod-shaped particles and dendritic particles having mesopores were prepared by the same methods as in the above-described Examples.

A 2 mg/ml NAD-GDH solution was prepared by using a nitrogen-purged 20 mM phosphate buffer (pH 7.4). To 1 ml of this NAD-GDH solution, 5 mg of hierarchical mesoporous silica synthesized by the above-described method was added. This mixture solution was stirred with a shaker at 4° C. for 20 hours to immobilize the GDH on the pore walls of the mesoporous silica. After the stirring, the solution was centrifuged at 20000 g for 10 minutes at 4° C. to obtain NAD-GDH-immobilizing silica. The amount of NAD-GDH adsorbed on the mesoporous silica was calculated by using absorption maxima of supernatants at 280 nm before and after the adsorption of NAD-GDH. The amount of adsorbed NAD-GDH was about 160 mg/g. The fact that the NAD-GDH was not adsorbed to the external surface of the mesoporous silica but adsorbed on the mesopore walls was confirmed by measuring a change in the adsorption behavior with respect to the mesopore walls in the nitrogen adsorption isotherm measurement of the dried NAD-GDH-immobilizing mesoporous silica.

Next, in order to evaluate thermal stability, 1 ml of a 20 mM phosphate buffer solution (pH 7.4) was added to 5 mg of the NAD-GDH-immobilizing mesoporous silica, and then the resulting mixture solution was heated at 90° C. for 30, 60, 90, or 120 minutes. After the heating, the mixture solution was centrifuged to obtain NAD-GDH-diaphorase-immobilizing silica. The obtained silica was washed twice with pure water. To this heated NAD-GDH-immobilizing silica, a 20 mM NAD solution prepared by using a 0.1 M tris-HCl buffer solution (pH 8.0) was added. After the stirring at room temperature for 5 minutes, a 1.5 M glucose solution was added to the silica solution. The resulting mixture solution was further stirred for 10 minutes. After the reaction, the solution was centrifuged at 20000 g for 10 minutes at 4° C. The activity of NAD-GDH for catalyzing a reduction reaction of NAD to NADH was measured by using the absorption maximum of NADH in the supernatant at 340 nm. For comparison, a solution of NAD-GDH that was not immobilized on mesoporous silica was prepared and similarly heated, and the activity of the NAD-GDH was measured. The relative activity of NAD-GDH was determined by using the absorbance of a solution obtained by adding 1.5 M of glucose to unheated NAD-GDH as a reference. The results confirmed the NAD-GDH immobilized on mesoporous silica retained a high relative activity even if the NAD-GDH was heated at 90° C. for 120 minutes. On the other hand, free NAD-GDH that was not immobilized on mesoporous silica was completely inactivated by heating at 90° C. for 30 minutes. The results suggest that NAD-GDH is prevented from thermal denaturation by being immobilized on pore walls of mesoporous silica.

Example 6

Comparison Behaviors of NAD-GDH and PQQ-GDH

In this Example, behavior of dendritic particles containing mesopores with immobilized PQQ-GDH or NAD-GDH in the measurement of a glucose solution containing maltose is investigated.

A 2 mg/ml of PQQ-GDH solution was prepared by using a nitrogen-purged 20 mM phosphate buffer (pH=7.4). To 1 ml of this PQQ-GDH solution, 5 mg of dendritic particles were added. This mixture solution was stirred with a shaker at 4° C. for 20 hours to adsorb the GDH on the pore walls of the mesoporous silica. After the stirring, the solution was centrifuged at 20000 g for 10 minutes at 4° C. to obtain PQQ-GDH-immobilizing silica. The amount of PQQ-GDH adsorbed on the mesoporous silica was calculated by using absorption maxima of supernatants at 280 nm before and after the adsorption of PQQ-GDH. The amount of the adsorbed PQQ-GDH was about 200 mg/g. The resulting PQQ-GDH-immobilizing silica was added to a 1 mM potassium ferricyanide solution, as an electron transfer material, prepared by using a 20 mM phosphate buffer solution.

In addition, NAD-GDH-diaphorase-immobilizing mesoporous silica was prepared by the same method as in the above-mentioned Example. A 10 mM VB solution was used as an electron transfer material.

These resulting PQQ-GDH-immobilizing silica and NAD-GDH-immobilizing silica were each added to 1 M glucose solutions containing maltose at various concentrations, and oxidation current was measured by cyclic voltammetry. In the silica immobilized with NAD-GDH, the current value was always constant independent of the maltose concentration. However, in the silica immobilized with PQQ-GDH, the current increased with the maltose concentration.

Based on these results in this Example, it was confirmed that NAD-GDH-immobilizing silica can be used in a glucose sensor that has a high specificity to glucose without the influence of maltose.

Example 7

Novel Method for Introducing NAD-GDH into Mesopores

In this Example, efficient introduction of NAD-GDH to the synthesized mesoporous silica is achieved by properly adjusting the salt concentration and the pH of a buffer solution.

A 2 mg/ml NAD-GDH solution was prepared by using a phosphate buffer solution (pH=7.4). The salt concentration of each buffer solution was adjusted to 0.1, 0.5, 1.0, 5.0, 10.0, or 20.0 mM. To 1 ml of this NAD-GDH aqueous solution, 5 mg of the dendritic particles synthesized in the above-mentioned Example was added. Each mixture solution was stirred with a shaker at 4° C. for 20 hours to adsorb the NAD-GDH on mesopore walls of the mesoporous silica. After the stirring, the solution was centrifuged at 20000 g for 10 minutes at 4° C. to prepare NAD-GDH-immobilizing silica at each salt concentration. The amount of NAD-GDH adsorbed on the mesoporous silica was calculated by using absorption maxima of supernatants at 280 nm before and after the adsorption of NAD-GDH. The fact that the GDH molecules in each solution were not adsorbed on the external surface of the mesoporous silica but adsorbed on the mesopore walls was confirmed by measuring a change in the adsorption behavior with respect to the mesopore walls before and after the adsorption of NAD-GDH to the mesoporous silica with a nitrogen adsorption measurement device.

The amount of NAD-GDH adsorbed on the pore walls increased in a curve pattern according to an increase in the salt concentration of the buffer solution. Thus, the Langmuir-type adsorption behavior was confirmed. When the 20 mM phosphate buffer solution was used, the maximum adsorption amount was 180 mg/g. In addition, a 5 mg/ml NAD-GDH aqueous solution was prepared by dissolving NAD-GDH in a 0.1 mM phosphate buffer solution so that the pH of the NAD-GDH aqueous solution is 8.0, which is near the isoelectric point of NAD-GDH, and a similar adsorption experiment was conducted by using this NAD-GDH aqueous solution. When the pH was 7.0, the amount of adsorbed NAD-GDH was about 80 mg/ml. When the pH was 8.0, the adsorption amount was 150 mg/ml, which was about twice that at the pH of 7.0.

The above-described results suggest that a reaction system in which electrostatic repulsion is relieved is required for efficiently introducing NAD-GDH into the mesopores. In addition, the results suggest that such a reaction system may be prepared by any methods, e.g., increasing the salt concentration of a buffer solution or adjusting the pH to about the isoelectric point of NAD-GDH. Herein, a method for increasing a salt concentration is the method for relieving the electrostatic repulsion between biological substances by increasing the concentration of a buffer solution and thereby increasing ionic strength in the reaction system. The method for introducing NAD-GDH into mesopores by controlling the salt concentration will be excellent, considering the fact that the optimum pH of NAD-GDH is about 7.0.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2005-375173 filed Dec. 27, 2005, which is hereby incorporated by reference herein in its entirety.

What is claimed is:

1. A porous material comprising mesopores,
    wherein the mesopores have a pore size of at least about 10 nm,
    wherein glucose dehydrogenase is immobilized in the mesopores,
    wherein the porous material has a dendritic skeleton, and
    wherein the mesopores extend through the dendritic skeleton in a direction crossing a longitudinal axis of the dendritic skeleton.

2. The porous material according to claim 1, wherein a length of the mesopores is not more than 30 times the pore size.

3. The porous material according to claim 1, wherein the pore size is from 10 to 30 nm.

4. The porous material according to claim 1, wherein the dendritic skeleton comprises branches, and macropores are formed by the branches that bind with each other or gaps between adjacent branches.

5. The porous material according to claim 1, wherein pore surfaces of the mesopores are formed of an organic substance.

6. The porous material according to claim 1, wherein the porous material is formed of silicon oxide, tin oxide, or titanium oxide.

7. The porous material according to claim 1, wherein pore size distribution determined by nitrogen gas adsorption analysis of the porous material has a single maximum value and more than 60% of a total number of the mesopores have the pore sizes within a 10 nm distribution range.

8. A composition comprising:
    a porous material according to claim 1; and
    an electron transfer material for receiving electrons from a biological substance in the porous material and transferring the electrons to an electrode.

9. A sensor comprising:
    the porous material according to claim 1;
    an electrode; and
    a buffer solution containing an electron transfer material for receiving electrons from a biological substance in the porous material and transferring the electrons to the electrode.

* * * * *